US00PP28646P2

(12) United States Plant Patent
van Sambeek

(10) Patent No.: US PP28,646 P2
(45) Date of Patent: Nov. 14, 2017

(54) ***PHLOX* PLANT NAMED 'BARPHFLARE'**

(50) Latin Name: *Phlox paniculata*
Varietal Denomination: Barphflare

(71) Applicant: Ellen van Sambeek, Aalsmeer (NL)

(72) Inventor: Ellen van Sambeek, Aalsmeer (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/330,229

(22) Filed: Aug. 27, 2016

(51) Int. Cl.
*A01H 5/02* (2006.01)

(52) U.S. Cl.
USPC ..... Plt./320

(58) Field of Classification Search
USPC ..... Plt./320
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Phlox* plant named 'Barphflare', characterized by its upright and mounding plant habit; vigorous growth habit; freely flowering habit; bright red-colored flowers; and good garden performance.

1 Drawing Sheet

Botanical designation: *Phlox paniculata.*
Cultivar denomination: 'BARPHFLARE'.

BACKGROUND OF THE INVENTION

The present invention relates to a new and distinct cultivar of *Phlox* plant, botanically known as *Phlox paniculata* and hereinafter referred to by the name 'Barphflare'.

The new *Phlox* plant is a product of a planned breeding program conducted by the Inventor in Aalsmeer, The Netherlands. The objective of the breeding program was to create new early and freely-flowering *Phlox* plants with attractive flower color.

The new *Phlox* plant originated from a cross-pollination made by the Inventor in July, 2013 in Aalsmeer, The Netherlands, of a proprietary selection of *Phlox paniculata* identified as code number PA11-000197-003, not patented, as the female, or seed, parent with a proprietary selection of *Phlox paniculata* identified as code number PA11-000228-001, not patented, as the male, or pollen, parent. The new *Phlox* plant was discovered and selected by the Inventor as a single flowering plant from within the progeny of the stated cross-pollination in a controlled environment in Aalsmeer, The Netherlands in July, 2014.

Asexual reproduction of the new *Phlox* plant by cuttings in a controlled environment in Aalsmeer, The Netherlands since March, 2015 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Barphflare'. These characteristics in combination distinguish 'Barphflare' as a new and distinct *Phlox* plant:

1. Upright and mounding plant habit.
2. Vigorous growth habit.
3. Freely flowering habit.
4. Bright red-colored flowers.
5. Good garden performance.

Plants of the new *Phlox* differ primarily from plants of the female parent selection in flower color as plants of the female parent selection have purple-colored flowers with white-colored centers.

Plants of the new *Phlox* differ primarily from plants of the male parent selection in flower color as plants of the male parent selection have purple-colored flowers with white-colored centers.

Plants of the new *Phlox* can be compared to plants of *Phlox paniculata* 'Sweet Summer', not patented. In side-by-side comparisons, plants of the new *Phlox* and 'Sweet Summer' differ in the following characteristics:

1. Plants of the new *Phlox* are more freely branching than plants of 'Sweet Summer'.
2. Plants of the new *Phlox* have smaller flowers than plants of 'Sweet Summer'.
3. Plants of the new *Phlox* and 'Sweet Summer' differ in flower color as plants of 'Sweet Summer' have white-colored flowers.
4. Plants of the new *Phlox* are more low temperature tolerant than plants of 'Sweet Summer'.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of typical flowering plant of 'Barphflare' grown in a container.

DETAILED BOTANICAL DESCRIPTION

The aforementioned photograph and following observations, measurements and values describe plants grown during the spring and early summer in 13-cm containers in a glass-covered greenhouse in Aalsmeer, The Netherlands and under cultural practices typical of commercial *Phlox* production. During the production of the plants, day temperatures averaged 21° C. and night temperatures averaged 15° C. Plants were pinched one time and were three months old when the photograph was taken and 14 months old when the description was taken. In the following description, color references are made to The Royal Horticultural Society Colour Chart, 2001 Edition, except where general terms of ordinary dictionary significance are used.

Botanical classification: *Phlox paniculata* 'Barphflare'.

Parentage:

*Female, or seed, parent*.—Proprietary selection of *Phlox paniculata* identified as code number PA11-000197-003, not patented.

*Male, or pollen, parent*.—Proprietary selection of *Phlox paniculata* identified as code number PA11-000228-001, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Thick, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright and mounding plant habit; vigorous growth habit.

*Plant height*.—About 40 cm to 45 cm.

*Plant width* (*spread*).—About 35 cm.

*Lateral branches*.—Length: About 45 cm. Internode length: About 2 cm. Strength: Strong. Aspect: Mostly upright. Texture: Smooth, glabrous. Color: Close to 144A.

Leaf description:

*Arrangement*.—Opposite, simple.

*Length*.—About 11 cm.

*Width*.—About 3.5 cm to 4.5 cm.

*Shape*.—Oblanceolate.

*Apex*.—Acute.

*Base*.—Attenuate.

*Margin*.—Finely serrate.

*Texture, upper and lower surfaces*.—Smooth, glabrous.

*Venation pattern*.—Pinnate, reticulate.

*Color*.—Developing leaves, upper surface: Close to 139A. Developing leaves, lower surface: Close to 137B. Fully expanded leaves, upper surface: Close to 139A; venation, close to 144C. Fully expanded leaves, lower surface: Close to 137C; venation, close to 144C.

*Petioles*.—Length: About 5 mm. Diameter: About 3 mm. Texture, upper and lower surfaces: Smooth, glabrous. Color, upper and lower surfaces: Close to 144D.

Flower description:

*Flower type and flowering habit*.—Single rotate and salverform flowers arranged in compound terminal and lateral panicles; flowers face mostly upright; freely flowering habit with about 50 to 60 flowers per inflorescence and about 350 flowers developing per plant during the flowering season.

*Fragrance*.—Slightly fragrant, pleasant.

*Natural flowering season*.—Plants begin flowering about 12 to 13 weeks after planting; plants flower naturally during July in The Netherlands; flowers persistent.

*Flower buds*.—Height: About 2.5 cm. Diameter: About 5 mm. Shape: Ovoid. Color: Close to 71B.

*Inflorescence height*.—About 20 cm.

*Inflorescence diameter*.—About 17 cm.

*Flower diameter*.—About 2.9 cm.

*Flower depth*.—About 2.2 cm.

*Flower throat diameter*.—About 3 mm.

*Flower tube length*.—About 2.2 cm.

*Flower diameter, proximally*.—About 2 mm.

*Petals*.—Quantity per flower: Typically five in a single whorl; petals fused at the base into a narrow tube. Lobe length: About 1.3 cm. Lobe width: About 1.5 cm. Lobe shape: Rounded. Lobe apex: Obtuse, emarginate. Lobe margin: Entire. Lobe texture, upper and lower surfaces: Smooth, glabrous. Throat texture: Smooth, glabrous. Tube texture: Pubescent. Color: When opening, upper surface: Close to 46C; towards the throat, blushed with close to 66A. When opening, lower surface: Close to 66C. Fully opened, upper surface: Close to 45C; towards the throat, blushed with close to 57A; venation, close to 45C; with development, color becoming closer to 67A. Fully opened, lower surface: Close to 80C; venation, close to 80C. Throat: Close to 72A; venation, close to 72A. Tube: Close to 71A; venation, close to 71A.

*Sepals*.—Quantity per flower: Typically five in a single whorl, fused towards the base; calyx, campanulate. Length: About 7 mm. Width: About 1 mm. Shape: Narrowly deltoid. Apex: Acuminate. Margin: Entire. Texture, upper and lower surfaces: Smooth, glabrous. Color: When opening and fully opened, upper surface: Close to 137C. When opening and fully opened, lower surface: Close to 137C.

*Peduncles*.—Length: About 10 cm. Diameter: About 2 mm. Strength: Moderately strong. Texture: Smooth, glabrous. Color: Close to 144A.

*Pedicels*.—Length: About 1 cm. Diameter: About 1 mm. Strength: Moderately strong. Texture: Pubescent. Color: Close to 143C.

*Reproductive organs*.—Stamens: Quantity per flower: Typically five. Filament length: About 0.5 mm. Filament color: Close to 155C. Anther length: About 2 mm. Anther color: Close to 8C. Pollen amount: Abundant. Pollen color: Close to 8B. Pistils: Quantity per flower: One. Pistil length: About 1.8 cm.

Stigma shape: Cleft, three-parted. Stigma color: Close to 8C. Style length: About 1.8 cm. Style color: Close to 144D. Ovary color: Close to 144A.

*Seeds and fruits*.—Seed and fruit development have not been observed on plants of the new *Phlox*.

Garden performance: Plants of the new *Phlox* have been observed to have good garden performance and tolerate rain, wind and frost.

Disease & pest resistance: Plants of the new *Phlox* have not been observed to be resistant to pathogens and pests common to *Phlox* plants.

It is claimed:

1. A new and distinct *Phlox* plant named 'Barphflare' as illustrated and described.

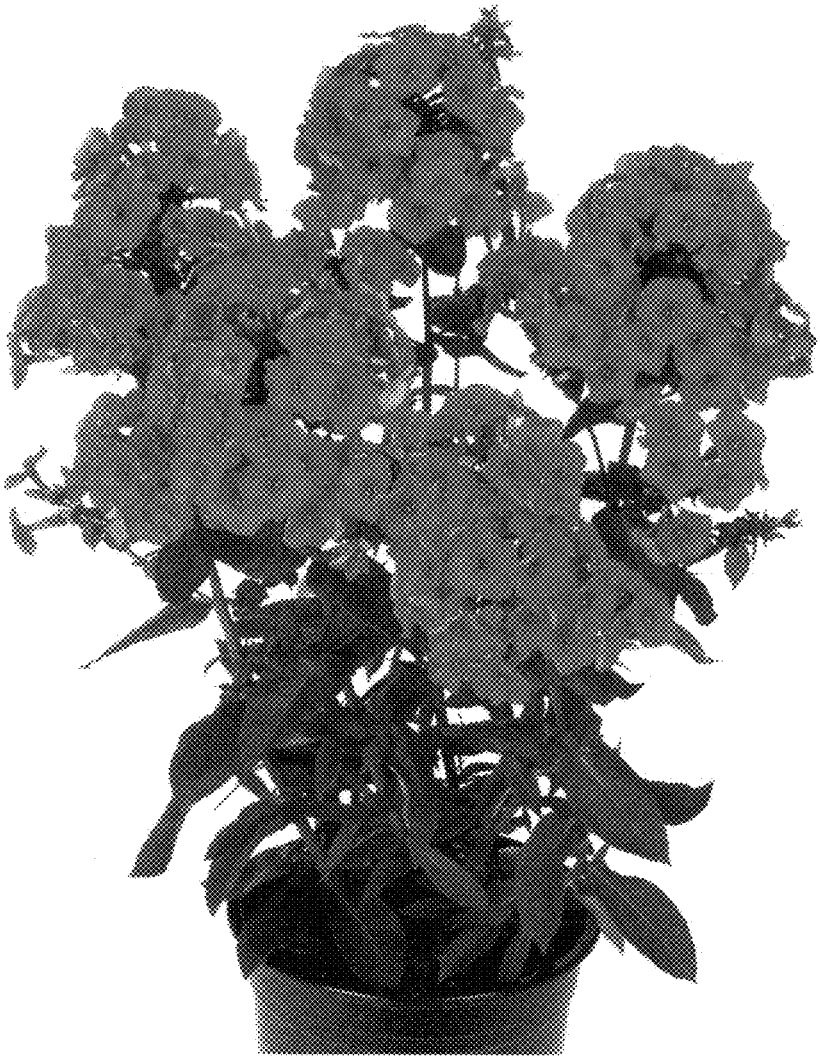

* * * * *